(12) United States Patent
Hossainy et al.

(10) Patent No.: US 6,860,946 B2
(45) Date of Patent: Mar. 1, 2005

(54) SYSTEM FOR THE PROCESS OF COATING IMPLANTABLE MEDICAL DEVICES

(75) Inventors: Syed F. A. Hossainy, Fremont, CA (US); Jeffrey Steward, Lakewood, CO (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/382,722

(22) Filed: Mar. 5, 2003

(65) Prior Publication Data

US 2003/0157241 A1 Aug. 21, 2003

Related U.S. Application Data

(62) Division of application No. 09/625,070, filed on Jul. 25, 2000, now Pat. No. 6,555,157.

(51) Int. Cl.[7] .......................... B05B 13/02; B05C 13/00
(52) U.S. Cl. ...................... 118/319; 118/320; 118/501; 118/52; 118/612
(58) Field of Search .............. 118/317–320, 52–53, 118/56, 612, 326, 500–501; 494/31, 34, 43, 17, 16, 20; 422/72, 101

(56) References Cited

U.S. PATENT DOCUMENTS

| | | | |
|---|---|---|---|
| 4,489,670 A | * 12/1984 | Mosser et al. ................. 118/55 |
| 4,616,593 A | * 10/1986 | Kawamura et al. ........... 118/303 |
| 5,342,621 A | 8/1994 | Eury .............................. 424/423 |
| 5,443,496 A | 8/1995 | Schwartz et al. .............. 623/1 |
| 5,464,650 A | 11/1995 | Berg et al. .................... 427/2.3 |
| 5,538,493 A | * 7/1996 | Gerken et al. ................. 494/16 |
| 5,605,696 A | 2/1997 | Eury et al. .................... 424/423 |
| 5,624,411 A | 4/1997 | Tuch .............................. 604/265 |
| 5,637,113 A | 6/1997 | Tartaglia et al. ............... 623/1 |
| 5,649,977 A | 7/1997 | Campbell ....................... 623/1 |
| 5,656,082 A | * 8/1997 | Takatsuki et al. ............. 118/52 |
| 5,700,286 A | 12/1997 | Tartaglia et al. ............... 623/1 |
| 5,707,385 A | 1/1998 | Williams ........................ 606/192 |
| 5,843,172 A | 12/1998 | Yan ................................ 623/1 |
| 5,897,911 A | 4/1999 | Loeffler ......................... 427/2.25 |
| 5,968,091 A | 10/1999 | Pinchuk et al. ............... 623/1 |
| 5,980,972 A | 11/1999 | Ding ............................. 427/2.24 |
| 6,013,099 A | 1/2000 | Dinh et al. ..................... 623/1 |
| 6,042,875 A | 3/2000 | Ding et al. .................... 427/2.24 |
| 6,056,993 A | 5/2000 | Leidner et al. ................ 427/2.25 |
| 6,140,127 A | 10/2000 | Sprague ......................... 435/395 |
| 6,153,252 A | 11/2000 | Hossainy et al. ............. 427/2.3 |
| 6,203,551 B1 | 3/2001 | Wu ................................ 606/108 |
| 6,517,889 B1 | 2/2003 | Jayaraman .................... 427/2.24 |
| 6,562,136 B1 | * 5/2003 | Chappa et al. ................ 118/500 |
| 6,605,154 B1 | * 8/2003 | Villareal ....................... 118/500 |

FOREIGN PATENT DOCUMENTS

| | | | |
|---|---|---|---|
| EP | 0627226 | 12/1994 | |
| EP | 0850651 | 7/1998 | |
| WO | WO 01/52772 A1 | 7/2001 | ............. A61F/2/06 |
| WO | 01/91918 | 12/2001 | |

* cited by examiner

Primary Examiner—Chris Fiorilla
Assistant Examiner—Yewebdar Tadesse
(74) Attorney, Agent, or Firm—Squire, Sanders & Dempsey L.L.P.

(57) ABSTRACT

Methods of coating an implantable device and a system for performing such methods are disclosed. An embodiment of the method includes applying a coating substance to the surface of an implantable device, and rotating the implantable device in a centrifuge. The method can uniformly coat the implantable device with the coating substance and to remove unwanted accumulations of coating substance entrained between struts or crevices in the implantable device body. This system is applicable to methods for coating intraluminal stents, synthetic grafts, and stent coverings with therapeutic compositions comprising therapeutic agents mixed with a polymeric matrix and a solvent.

24 Claims, 3 Drawing Sheets

SYSTEM FOR THE PROCESS OF COATING IMPLANTABLE MEDICAL DEVICES

CROSS REFERENCE

This is a divisional application of U.S. Ser. No. 09/625,070, issued as U.S. Pat. No. 6,555,157, which was filed on Jul. 25, 2000.

FIELD OF THE INVENTION

The present invention relates to the coating of an implantable device. More specifically, this invention relates to a centrifuge system and method for coating of an intraluminal implantable device, such as a stent.

BACKGROUND

Occlusion of blood vessels reduces or blocks blood flow. During the course of atherosclerosis, for example, growths called plaques develop on the inner walls of the arteries and narrow the bore of the vessels. An emboli, or a moving clot, is more likely to become trapped in a vessel that has been narrowed by plaques. Further, plaques are common sites of thrombus formation. Together, these events increase the risk of heart attacks and strokes.

Traditionally, critically stenosed atherosclerotic vessels have been treated with bypass surgery in which veins removed from the legs, or small arteries removed from the thoracic cavity, are implanted in the affected area to provide alternate routes of blood circulation. More recently, implantable devices, such as synthetic vascular grafts and stents, have been used to treat diseased blood vessels.

Synthetic vascular grafts are macro-porous vessel-like configurations typically made of expanded polytetrafluoroethylene (ePTFE), polyethylene terephthalate (PET), polyurethane (PU), or an absorbable polymer. Grafts made of ePTFE or PET are very non-wetting materials when introduced into an aqueous environment, causing difficulty in impregnating the materials. In addition, grafts made of ePTFE or PET typically are permanently implanted in the body, while grafts made of an absorbable polymer bioabsorb over time. A graft may be positioned into the host blood vessel as a replacement for a diseased or occluded segment that has been removed. Alternatively, a graft may be sutured to the host vessel at each end so as to form a bypass conduit around a diseased or occluded segment of the host vessel.

Percutaneous transluminal coronary angioplasty (PTCA) is a procedure for treating heart disease in which a catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

Restenosis of the artery commonly develops over several months after the procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of medial smooth muscle cells. Excessive neoinitimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

Intravascular stents are sometimes implanted within vessels in an effort to maintain the patency thereof by preventing collapse and/or by impeding restenosis. Implantation of a stent is typically accomplished by mounting the stent on the expandable portion of a balloon catheter, maneuvering the catheter through the vasculature so as to position the stent at the desired location within the body lumen, and inflating the balloon to expand the stent so as to engage the lumen wall. The stent automatically locks into its expanded configuration, allowing the balloon to be deflated and the catheter removed to complete the implantation procedure. A covered stent, in which a graft-like covering is slip-fit onto the stent, may be employed to isolate the brittle plaque from direct contact with the stent, which is rigid.

To reduce the chance of the development of restenosis, therapeutic substances may be administered to the treatment site. For example, anticoagulant and antiplatelet agents are commonly used to inhibit the development of restenosis. In order to provide an efficacious concentration to the target site, systemic administration of such medication may be used, which often produces adverse or toxic side effects for the patient. Local delivery is a desirable method of treatment, in that smaller total levels of medication are administered in comparison to systemic dosages, but are concentrated at a specific site. Therefore, local delivery may produce fewer side effects and achieve more effective results.

One commonly applied technique for the local delivery of a therapeutic substance is through the use of a medicated implantable device, such as a stent or graft. Because of the mechanical strength needed to properly support vessel walls, stents are typically constructed of metallic materials. The metallic stent may be coated with a polymeric carrier, which is impregnated with a therapeutic agent. The polymeric carrier allows for a sustained delivery of the therapeutic agent.

Various approaches have previously been used to join polymers to metallic stents, including dipping and spraying processes. In one technique, the stent is first formed in a flat sheet, placed in a solution of polyurethane, and heated for a short period of time. Additional polyurethane solution is applied on top of the flat sheet, and the stent is again heated. This process produces a polyurethane film over the surface of the stent, and excess film is manually trimmed away. In one variation of this technique, microcapsules containing therapeutic agents are incorporated into the polyurethane film by adding the microcapsules to the polyurethane solution before heating.

In another technique, a solution is prepared that includes a solvent, a polymer dissolved in the solvent, and a therapeutic agent dispersed in the solvent. The solution is applied to the stent by spraying the solution onto the stent using an airbrush. After each layer is applied, the solvent is allowed to evaporate, thereby leaving on the stent surface a coating of the polymer and the therapeutic substance. Use of this spraying technique to apply a thick coating may result in coating uniformity problems, so multiple application steps are sometimes used in an attempt to provide better coating uniformity.

In yet another coating technique, a solution of dexamethasone in acetone is prepared, and an airbrush is used to spray short bursts of the solution onto a rotating wire stent. The acetone quickly evaporates, leaving a coating of dexamethasone on the surface of the stent.

The above-described methods often fail to provide an economically viable method of applying an even coating on the stent surfaces. One common result when using these spraying or immersion processes is that the aqueous coating tends to collect in crevices, apertures, or cavities in the framework of the stent, resulting in an uneven coating having an uncontrollably variable coating thickness. In particular, an excess amount of coating is often entrained in the angle between two intersecting struts of a stent, which is sometimes called "webbing" or "pooling." The deposition of excessive amounts of therapeutic agents results in a poor surface area to volume ratio relative to conformal coatings. When such a coating experiences uncontrolled drying, drying artifacts may result in drug crystal formation.

The use of multiple applications of a fine, diffuse spray may produce a more controllable, even coating than immersion techniques. However, the diffuse application results in much of the coating substance not coating the stent and instead being released into the air. This inefficient use of the coating substance wastes the coating substance, which may be quite expensive, and increases the exposure of the air brush operator to the coating substance.

Accordingly, there is a need for an improved method for coating medical devices which produces superior coating uniformity without an excessive loss of materials.

SUMMARY

In accordance with an aspect of the present invention, a method for coating a implantable device includes applying a coating substance on a surface of said implantable device, and rotating said implantable device about an axis of rotation. A centrifuge system may be used to rotate the prosthesis. The implantable device may be a stent, graft, or stent covering. The coating substance may be applied using a variety of techniques, including immersion or spraying, among other possibilities. The method may further include collecting runoff coating substance in a runoff reservoir of the centrifuge system while rotating the implantable device. This collected runoff coating substance may then be recycled and used to coat a second implantable device, thus avoiding waste of the coating substance.

Another embodiment of the present invention includes a centrifuge system for coating an implantable device. The centrifuge system includes a rotor having an axis of rotation, said rotor including a plurality of chambers. A motor is operably connected to said rotor for rotating said rotor. A plurality of centrifuge containers are each received in one of said plurality of chambers in said rotor. A plurality of mandrels are each mounted in one of said plurality of centrifuge containers and adapted to receive an implantable device.

Embodiments of the present invention can be used to coat a variety of implantable devices with aqueous or solvent-based coating substances. In particular, certain embodiments can be used to coat stents with therapeutic or bioactive substances, such as compositions of a polymer, solvent, and therapeutic substance.

BRIEF DESCRIPTION OF THE DRAWINGS

The present invention may be better understood, and its numerous objects, features, and advantages made apparent to those skilled in the art, by referencing the accompanying drawings.

The use of the same reference symbols in different drawings indicates similar or identical items.

DETAILED DESCRIPTION

Figure 1:
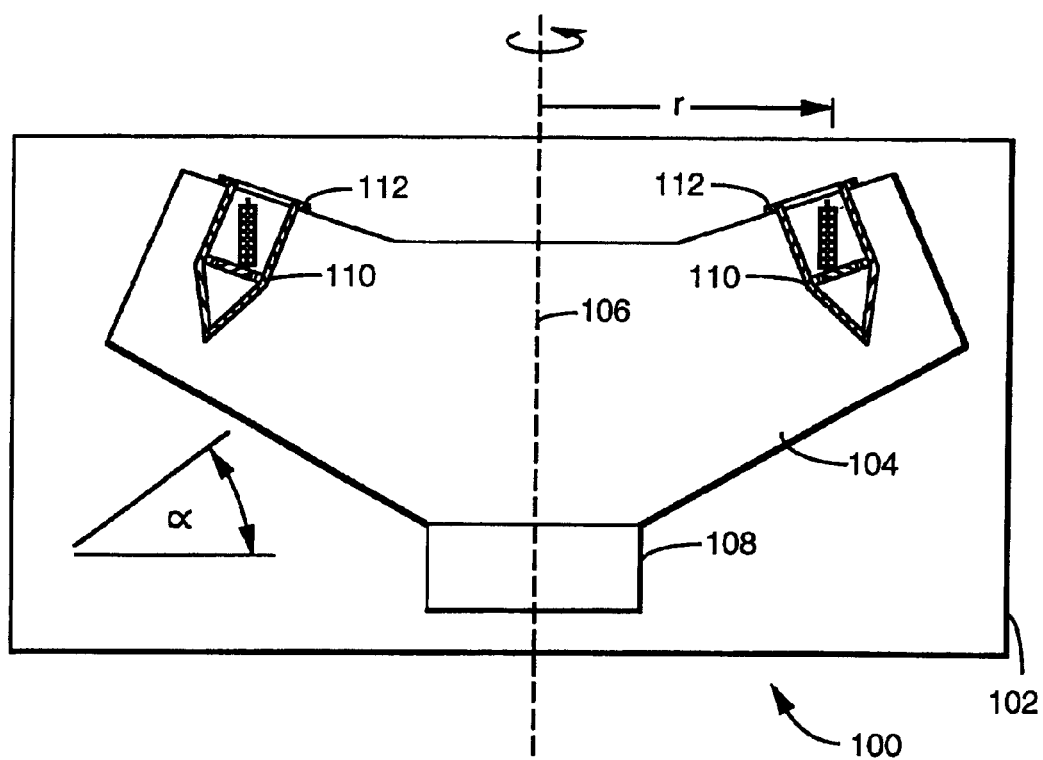
FIG. 1 illustrates in plan view a cross-section of a centrifuge system in accordance with an embodiment of the present invention.

The following description is meant to be illustrative only and not limiting. Other embodiments of this invention will be apparent to those of ordinary skill in the art in view of this description.

The figures generally illustrate the techniques used to apply coatings to a stent in accordance with an embodiment of the present invention. Although the illustrated and described embodiments may relate to wire-based stents, any of a variety of implantable devices may be subjected to the coating process described herein, including, but not limited to, wire-based stents, tubular stents, rolled-sheet type stents, stent coverings, vascular grafts, or any implantable device having a complicated architecture which is not amenable to standard coating.

The materials from which such stents are formed may include metals such as, but not limited to, stainless steel, "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The stent also may be made from virtually any bio-compatible material, such as bioabsorbable or biostable polymers.

Vascular grafts may be used to replace, bypass, or reinforce diseased or damaged sections of a vein or artery. These grafts can be made from any suitable material including, but not limited to, highly open-pored materials such as polymers of expanded polytetrafluoroethylene (ePTFE) and polyethylene terephthalate (PET), or less porous materials such as polyurethanes, absorbable polymers, and combinations or variations thereof. Grafts may be formed using a lyophilization process. Polyurethanes from which the graft may be made include, but are not limited to, Biomer, Biospan, and Elastion. Absorbable polymers from which the graft may be made include, but are not limited to, polycaprolactone (PCL), poly(lactic acid) (PLA), poly(glycolic acid) (PGA), polyanhydrides, polyorthoesters, polyphosphazenes, and components of extracellular matrix (ECM). In such an embodiment, additional interstices can be formed in the graft by any conventional methods known to one of ordinary skill in the art, including exposure of the graft to a laser discharge to form a pattern of pores.

In other embodiments, the implantable device to be coated is a covering for a self-expandable or balloon-expandable stent. This covering can be formed of materials similar to those from which the above-described graft may be formed.

Various types of coating substances may be applied to an implantable device in accordance with the present invention.

In one embodiment, the coating substance includes a polymer loaded with a therapeutic substance. The terms "polymer," "poly," and "polymeric" as used herein mean the product of a polymerization reaction and are inclusive of homopolymers, copolymers, terpolymers, etc., whether natural or synthetic, including random, alternating, block, graft, crosslinked, blends, compositions of blends and variations thereof. The term "pre-polymer" refers to a reactive polymer that has not yet been crosslinked.

The polymer or combination of polymers can be applied to a stent based on the polymer's or polymers' ability to carry and release, at a controlled rate, various therapeutic agents such as antithrombogenic or anti-proliferative drugs. The polymeric material is most suitably bio-compatible, including polymers that are non-toxic, non-inflammatory, chemically inert, and substantially non-immunogenic in the applied amounts. The polymer is typically either bioabsorbable or biostable. A bioabsorbable polymer breaks down in the body and is not present sufficiently long after implantation to cause an adverse local response. Bioabsorbable polymers are gradually absorbed or eliminated by the body by hydrolysis, metabolic process, or bulk or surface erosion. Examples of bioabsorbable materials include but are not limited to polycaprolactone (PCL), poly-D, L-lactic acid (DL-PLA), poly-L-lactic acid (L-PLA), poly(lactide-co glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch, and collagen are typically also suitable. Examples of biostable polymers include Parylene® and Parylast® (available from Advanced Surface Technology of Billerica, Mass.), polyurethane, such as a segmented polyurethane solution containing a dimethylacetamide (DMAc) solvent developed by the Polymer Technology Group, Inc. of Berkeley, Calif., and known by the trade name BioSpan®, polyethylene, polyethlyene teraphthalate, ethylene vinyl acetate, silicone and polyethylene oxide (PEO).

The expression "therapeutic agent" as used herein broadly refers to an agent or substance that possesses desirable therapeutic characteristics. The therapeutic agent may be, for example, antineoplastic, antimitotic, antiinflammatory, antiplatelet, anticoagulant, antifibrin, antithrombin, antiproliferative, antibiotic, antioxidant, and antiallergic substances, as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co., Stamford, Conn.). Examples of such antiplatelets, anticoagulants, antifibrins, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone.

While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed embodiments. For example, while many of the herein-described therapeutic agents have been used to prevent or treat restenosis, they are provided by way of example and are not meant to be limiting, since other drugs or coatings may be developed which are equally applicable for use with embodiment of the present invention.

In other embodiments, the coating is an aqueous solution of a therapeutic substance that does not contain a polymer matrix, such as, for example, an aqueous solution of heparin. This aqueous solution can be applied to the stent in accordance with the present invention and allowed to dry, thereby forming a heparin coating on the stent.

In addition to a polymer and a therapeutic agent, the coating substance may also include a solvent. The solvent can be virtually any solvent that is compatible with the implantable device to be coated. Examples of suitable solvents include but are not limited to dimethyl sulfoxide, dimethyl formamide, tetrahydroforan, dimethyl acetamide, trichloroethane, acetone, ethanol, methanol, isopropanol, and ethyl acetate.

FIG. 1 shows a cross-section of an exemplary centrifuge system 100 in accordance with an embodiment of the present invention. Centrifuge system 100 includes a centrifuge device 102, which includes a rotatable rotor 104 for rotation about an axis 106, and a motor 108 which drives rotor 104 to rotate about axis 106. Centrifuge models 5410, 5415, 5417, 5804, and 5810, sold by Eppendorf Scientific, Inc., of Westbury, N.Y., may be used, for example, as centrifuge device 102. Exemplary centrifuge devices 102 provide rotational speeds of up to, for example, 14,000 rotations per minute ("RPM"). Rotor 104 includes a plurality of hollow chambers 110 circularly arranged about axis 106. Each chamber 110 is sized to receive a centrifuge container 112. Various centrifuge devices 102 available on the market are capable of centrifuging large numbers of centrifuge containers 112 simultaneously.

Figure 2:
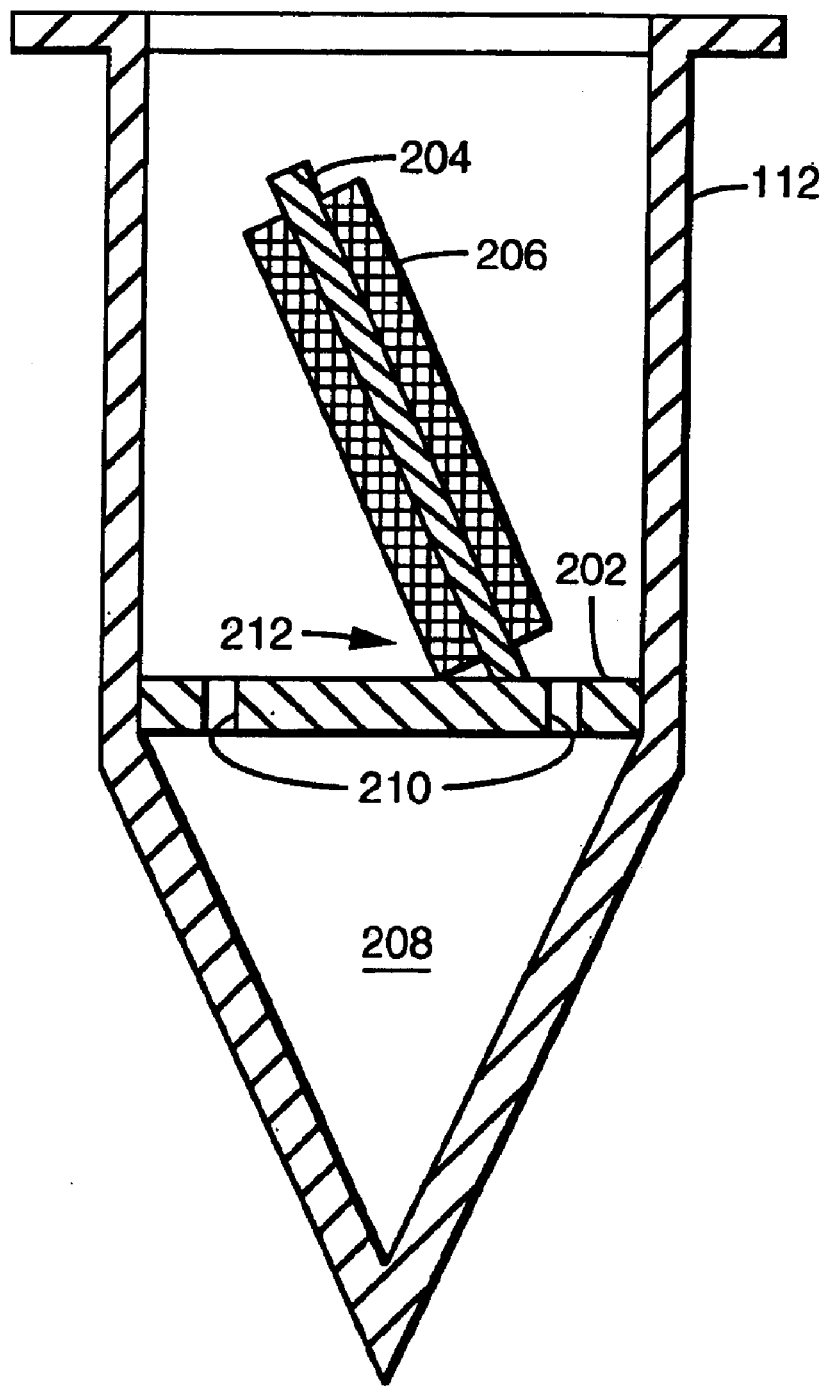
FIG. 2 is a cross-section in plan view of a centrifuge container in accordance with an embodiment of the present invention.

FIG. 2 shows in greater detail a cross-section of an exemplary centrifuge container 112. Centrifuge container 112 can be formed using a conventional centrifuge tube that has been modified as described below. A support 202 is provided towards the bottom of centrifuge container 112, and a mandrel 204 is mounted thereon. In this embodiment, mandrel 204 is a rod. Mandrel 204 is inserted into the interior of the implantable device to be coated, such as a cylindrical stent 206. Mandrel 204 holds stent 206 and prevents stent 206 from contacting the interior walls of centrifuge container 112. Support 202 separates stent 206 from runoff reservoir 208, which is provided at the bottom of centrifuge container 112. Drainage openings 210 may be provided in support 202.

As can be seen in the embodiment shown in FIGS. 1–2, mandrel 204 is tilted such that when each centrifuge container 112 is mounted in centrifuge system 100, stents 206 are positioned such that their longitudinal axes are nearly parallel to axis of rotation 106. This may provide a more even coating on stents 206 after centrifugation. In alternative embodiments, mandrels 204 may have a different tilt angle relative to the central axes of centrifuge containers 112, or may have no tilt at all.

Figure 3:
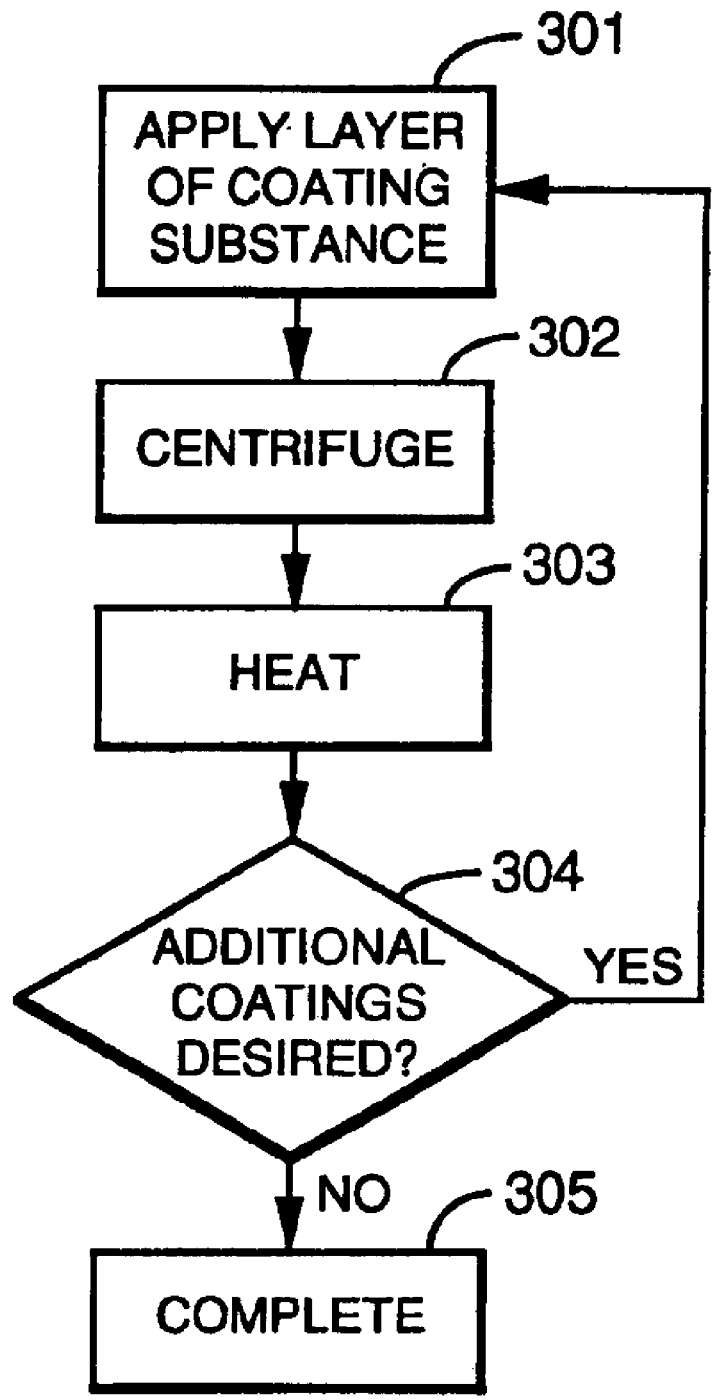
FIG. 3 is a flowchart of a coating process in accordance with an embodiment of the present invention.

FIG. 3 is a flowchart illustrating an exemplary method of coating an implantable device in accordance with an embodiment of the present invention. For the sake of example, the implantable device described with respect to FIGS. 1–3 is a stent, but the method also may be applied to various other implantable devices discussed above.

In act 301, a first coating is applied to stent 206. The coating may be applied by spraying or immersing stent 206 with an aqueous coating substance using techniques similar to those described in the background section above. The term "aqueous" as used herein refers to substances having sufficient fluidity such that the substance can flow over the surface of stent 206 when processed through the further acts described below. "Aqueous" is not intended to limit the coating substance to water-based substances or to low viscosity materials. Even highly viscous substances such as a hyaluronic acid solution (e.g., 1% hyaluronic acid), high molecular weight polyethylene glycol solution, gelatin solution, or poly (lactic) acid in 1, 1, 2 trichloroethane (e.g., 10% poly (lactic) acid) are included within the term.

As with conventional coating techniques, the spraying or immersion of stent 206 in the coating substance typically results in a non-uniform coating, with webbing being observable between struts on stent 206. In act 302, the still-wet stent 206 is inserted onto mandrel 204 in centrifuge container 112 such that mandrel 204 extends through the hollow interior of stent 206. Centrifuge container 112 is then inserted into chamber 110 of centrifuge system 100 (FIG. 1), and centrifuge system 100 is used to rotate stent 206 about axis 106 at high speeds. Centrifuge system 100 includes a plurality of rotatable chambers 110, such that multiple coated stents 206 can be centrifuged simultaneously, thereby increasing processing throughput.

The rotation of chambers 110 at high speeds creates a centrifugal force upon the coating substance that previously was applied to the surface of stent 206. This centrifugal force causes excess accumulations of coating substance, particularly the portions entrained between the struts of stent 206, to be more evenly redistributed over stent 206. This redistribution of the coating substance over the surface of stent 206 provides a more uniform coating free of webbing.

The centrifugation of stent 206 may result in some excess coating substance being removed from the surface of stent 206. Drainage openings 210 are provided in support 202 so that the runoff coating substance can flow from the upper portion of centrifuge container 112 into runoff reservoir 208. The channeling of runoff coating substance into runoff reservoir 208 prevents the coating substance from accumulating at the bottom end 212 of stent 206, which could lead to a non-uniform coating. This runoff coating substance can be recovered from runoff reservoir 208 and reused to coat additional stents 206. The recycling of the coating substance can produce significant cost savings when an expensive therapeutic agent is being used.

In alternative embodiments, different structures are provided to effectuate the flow of runoff coating substance into runoff reservoir 208. In one embodiment, support 202 is square-shaped, such that when support 202 is fitted into a centrifuge container 112 which is cylindrical in shape, runoff coating substance can flow around the openings formed between the edges of square support 202 and the circular interior of centrifuge container 112. In another embodiment, support 202 comprises a mesh platform, such that fluid can freely flow through support 202 to pass into reservoir 208. Numerous other variations are possible.

In act 303, coated, centrifuged stent 206 is immediately placed into a convention oven for heating. This heating evaporates solvents that might be present in the coating substance, thereby forming a solid coating on the surface of stent 206. Heating act 303 can improve the adhesion of the coating substance to the metal forming metallic stents 206, and can also provide a better equilibrium for the solid phase drug distribution in the matrix of the coating substance. Heating act 303 might be used, for example, when coating stent 206 with a composition of ethylene vinyl alcohol copolymer with dimethyl sulfoxide, as will be described in greater detail in the example below. In alternative embodiments, no heating act is used, and stent 206 may be implanted immediately after centrifugation act 302. The use of a heating step, and the parameters of such a step will vary with the application.

In act 304, it is determined whether one or more additional layers of coating substance is to be applied to stent 206. If so, the process returns to act 301, and another layer of coating substance is applied. Multiple layers of coating substance may be applied in order to produce a more uniform coating with fewer defects. Each layer can be formed very thin and uniform, and subsequent layers can be added to increase the overall loading onto stent 206. Moreover, the use of multiple layers can provide enhanced control over the release rate of the coating. Finally, when the desired number of layers have been applied, the process is completed at act 305, and stent 206 may be packaged for delivery or immediately implanted into a patient's body using techniques well-known to those of ordinary skill in the art.

Grafts and stent coverings may include a large number of interstices, which cause these devices to have a generally permeable characteristic. In accordance with various embodiments of the present invention, permeable grafts and stent coverings can be coated with a coating substance, such as those described above, and then placed into a centrifuge for centrifugation. The centrifugation process provides can provide improved perfusion of the coating substance through the interstices of the graft or stent covering, particularly when the devices are formed of a highly hydrophobic material.

In another embodiment, a process for applying a hydrogel coating to a graft or stent covering is provided. When applying a hydrogel coating, a coating substance containing at least one crosslinkable pre-polymer and a first fluid in which the pre-polymer is soluble is prepared. The pre-polymer should be in true solution, saturated, or super-saturated with the first fluid. Exemplary crosslinkable pre-polymers include, but are not limited to, polyethylene glycol (PEG) diacrylate, hyaluronic, and pluronic. The concentration of pre-polymer in the composition should be selected such that it is high enough to ensure effective crosslinking of the pre-polymer since a solution too dilute may not form a crosslinked hydrogel. An implantable device may then be dipped into this pre-polymer coating substance. Alternatively, prior to application of the pre-polymer, the implantable device may be perfused with a low surface energy solvent such as, for example, acetone or ethanol, which effectuates improved perfusion of the pre-polymer solution through the interstices of the implantable device.

After the implantable device is dipped into the pre-polymer solution, the implantable device is placed in a centrifuge container and loaded into a centrifuge system, similar to the centrifuge container 112 and centrifuge system 100 described above. Centrifuging the coated implantable device spreads the viscous pre-polymer solution evenly across the surface of the implantable device and into the interstices or crevices therein.

Finally, the pre-polymer is cured to form a hydrogel coating on the implantable device. Curing may be accomplished photochemically using ultraviolet or visible irradiation and a photoinitiator, thermally, or by moisture curing at room temperature. The practice of these and other suitable curing procedures is well known to those of ordinary skill in the art.

In yet another embodiment, the coating method of the present invention can be used to provide a physician with greater flexibility in selecting a desired coating substance for use with a particular patient. Conventionally, stents are coated by either the stent manufacturer or a third party prior to delivering the stent to a physician for implantation into a patient. In accordance with the present invention, a physician can apply a coating on a bare stent, centrifuge the stent using a small, portable centrifuge device, and implant the freshly-prepared stent in a patient's body. This enables the physician to precisely select the composition of the coating substance applied to the stent. In addition, because the stent can be locally coated and then immediately implanted by the physician after coating, perishable or environmentally-sensitive materials may be used to coat the stent.

EXAMPLE

In one example, fifteen 13 mm ACS Multi-Link Duet® stainless steel stents, produced by the Guidant Corp. of Indianapolis, Ind., are immersed (e.g., for a few seconds or up 20 seconds or more) in a coating substance including ethylene vinyl alcohol copolymer (commonly known by the generic name EVOH or by the trade name EVAL) and dimethyl sulfoxide ("DMSO") solvent, in a 1:4 ratio. Tetrahydrofuran (THF) may be included in the DMSO. The THF lowers the viscosity of the coating substance and increases wetting on the surface of stent 206. Each of the fifteen stents is then immediately mounted into a centrifuge container 112, as described above with respect to FIGS. 1–3. The fifteen centrifuge containers 112 are inserted into chambers 110, and centrifuge containers 112 are rotated for 60 seconds at 6,500 RPM.

The stents are then removed from centrifuge containers 112, placed on mandrels, and loaded into a Blue M model vacuum convection oven from the Blue M Electric company of Watertown, Wis., for 24 hours at a temperature of 65° C. The heating causes the DMSO in the coating substance to fully evaporate, leaving a thin coating of EVOH on the stents. Alternative forms of heating may also be used, such as the use of a "hot plate" heating surface.

Next, the immersion, centrifugation, and heating acts can be replaced (e.g., up to four times or more), depending on the thickness of coating desired. For theses subsequent processes, the stents are immersed in the 1:4 solution of EVOH and DMSO.

The above-described process results in a white, frosty coating on the test stents. After two coating cycles, the weight of the coating deposited on the stents ranged from approximately 0.066–0.080 mg and the thickness ranged from approximately 0.5 to 1.5 $\mu$m.

The rotational speed during centrifugation can be varied. Higher RPM values may provide improved uniformity and a reduction in defects. However, lower RPM values may improve solid uptake, i.e., the total loading of the coating substance onto stent 206. The solid uptake is calculated by measuring the initial weight of stent 206, and then measuring the weight after the loading and centrifugation acts. Increasing the total centrifugation time may also improve the uniformity and reduce defects in the coating. Accordingly, practitioners should tailor the process to the particular application.

Embodiments of the present invention enable highly viscous materials to be coated onto implantable devices. Viscous materials are not usually amenable to conventional coating methods such as dipping or spraying, because of the viscous material's propensity to accumulate in an uneven layer. However, the addition of a centrifugation step after dipping the implantable device in the viscous coating material can transform the uneven masses into a smooth, even coating.

Embodiments of the present invention also enable uniform coatings to be applied to implantable devices with improved repeatability, thereby improving coating uniformity between batches of implantable devices. With conventional manually-applied spray-coating techniques, operator error or inconsistency may result in different coating thicknesses between batches of stents. The centrifugation processes can reduce unwanted gross deposition of coating substances and enable high reproducibility of the coating quality.

Embodiments of the present invention also enable multiple stents to be processed simultaneously. Unlike manually-applied airbrush coating methods, in which stents are coated individually or in small groups, large batches of stents can be simultaneously immersed in the coating solution, simultaneously rotated in the centrifuge device, and simultaneously heated in an oven, thereby increasing throughput.

Embodiments of the present invention also may improve operator safety when coating implantable devices with hazardous materials. It is generally not desirable to spray coat an implantable device with toxic or radioactive coating substances, because of the increased exposure of the operator to the airborne hazardous coating substance. Dipping and centrifuging the implantable device as described above can decrease the amount of handling required for the coating process, resulting in less environmental contamination.

Embodiments of the present invention may also reduce defects due to handling of the implantable device. In conventional spray processes, the implantable device is held aloft using one or two clamps or fixtures while the coating substance is sprayed onto the device. The point where these clamps contact the device may result in defects in the coating. In contrast, the centrifuge container 112 results in minimal contact with the implantable device during the centrifuge process.

The above embodiments only illustrate the principles of this invention and are not intended to limit the invention to the particular embodiments described. For example, the heating acts used to evaporate the solvent material may be omitted, and other embodiments utilizing centrifugation coating methods can be used in combination with other acts in different processes which do not require active heating. These and various other adaptations and combinations of features of the embodiments disclosed are within the scope of the invention, as defined by the following claims.

What is claimed is:

1. A centrifuge system to coat an implantable medical device with a composition, comprising:
    a rotor having an axis of rotation, the rotor including a plurality of chambers;
    a motor operably connected to the rotor for rotating the rotor;
    a plurality of centrifuge containers, each centrifuge container being received in one of the plurality of chambers in the rotor; and
    a plurality of mandrels, wherein a mandrel is mounted in each of the plurality of centrifuge containers and adapted to support an implantable medical device.

2. The centrifuge system of claim 1, wherein each of the centrifuge containers comprises:
    a runoff reservoir region provided at a bottom of the centrifuge containers to collect excess composition that is discharged from the implantable medical devices wherein the mandrels support the implantable medical devices above the runoff reservoir regions.

3. The centrifuge system of claim 1, wherein the mandrels are adapted to receive a stent.

4. The centrifuge system of claim 1, wherein the mandrels are adapted to receive a graft.

5. The centrifuge system of claim 1, wherein the mandrels are adapted to receive a stent covering.

6. An apparatus to coat a stent having a composition disposed thereon, comprising:
    a rotor having a compartment, wherein the compartment has a first section, a second section, a divider separating the first section from the second section, and a mandrel disposed within the first section of the compartment to receive the stent.

7. The apparatus of claim 6, wherein the mandrel is positioned within the compartment so as to prevent an outer surface of the stent from contacting an inner surface of the compartment.

8. The apparatus of claim 6, wherein the stent is securely positioned on the mandrel in the first section, and the second section is adapted to collect any excess composition discharged off the stent.

9. The apparatus of claim 6, wherein the divider includes an opening or a mesh portion for allowing the composition to be collected in the second section of the compartment.

10. The apparatus of claim 6, wherein the compartment additionally includes a drainage opening to allow the composition to be collected in the second section of the compartment.

11. A compartment in which implantable medical device can be supported during the process of forming a coating on the device, comprising:
    a first section;
    a run-off section disposed below the first section to collect a coating material; and
    a support to hold the device in the first section and above the run-off section during the process of forming a coating on the device.

12. The compartment of claim 11, wherein the compartment is a part of a rotating apparatus.

13. The compartment of claim 11, wherein the compartment is adapted to be used with a rotating apparatus.

14. The compartment of claim 11, additionally including a divider separating the first section from the run-off section.

15. The compartment of claim 11, additionally including a divider positioned between the first section and the run-off section, wherein the support to hold the device is coupled to the divider.

16. The compartment of claim 11, wherein the device is a stent and wherein the support is a mandrel adapted to be inserted into the stent.

17. An apparatus used in the process of forming a coating on an implantable medical device, comprising:
    a rotor having a compartment to house an implantable medical device, wherein the compartment is tilted with respect to a horizontal plane; and
    a mandrel positioned inside of the compartment to support the device during the rotation of the rotor such that the positioning of the mandrel inside of the compartment prevents an outer surface of the device from making contact with an inner surface of the compartment during rotation of the rotor.

18. The apparatus of claim 17, wherein the longitudinal axis of the mandrel is aligned in parallel to an axis about which the rotor can be rotated.

19. The apparatus of claim 17, wherein the longitudinal axis of the mandrel is aligned in parallel to and positioned at a distance away from an axis of rotation of the rotor.

20. The apparatus of claim 17, wherein the compartment includes a run-off section positioned below the mandrel for receiving a coating substance that has been applied to the device.

21. The apparatus of claim 17, wherein the mandrel is in a vertical position at a generally 90 degree angle from the horizontal plane.

22. The apparatus of claim 6, wherein the mandrel is supported by the divider.

23. The compartment of claim 11, wherein the device is a stent, a graft or a stent covering.

24. The apparatus of claim 17, wherein the device is a stent, a graft or a stent covering.

* * * * *